(12) United States Patent
de Paoli Ambrosi

(10) Patent No.: US 7,169,811 B2
(45) Date of Patent: Jan. 30, 2007

(54) COMPOSITION BASED ON ETHYL ESTER OF LINOLEIC ACID AND TRIETHYL ESTER OF CITRIC ACID FOR TOPICAL USE IN THE TREATMENT OF SEBORRHEA AND ACNE

(75) Inventor: Gianfranco de Paoli Ambrosi, Salo (IT)

(73) Assignee: General Topics S.r.l. (IT)

( * ) Notice: Subject to any disclaimer, the term of this patent is extended or adjusted under 35 U.S.C. 154(b) by 572 days.

(21) Appl. No.: 10/322,566

(22) Filed: Dec. 16, 2002

(65) Prior Publication Data

US 2003/0118623 A1    Jun. 26, 2003

(30) Foreign Application Priority Data

Dec. 20, 2001    (IT)    ............... BS2001A0111

(51) Int. Cl.
*A61K 31/215*    (2006.01)
*A61K 31/21*    (2006.01)

(52) U.S. Cl. .................................... 514/529; 514/506
(58) Field of Classification Search ................ 514/557
See application file for complete search history.

(56) References Cited

U.S. PATENT DOCUMENTS 6,028,067 A * 2/2000 Hong et al. ................. 514/200
6,267,985 B1 * 7/2001 Chen et al. ................. 424/451

* cited by examiner

*Primary Examiner*—Sreenivasan Padmanabhan
*Assistant Examiner*—Jennifer Kim
(74) *Attorney, Agent, or Firm*—McGlew & Tuttle, PC

(57) ABSTRACT

The present invention relates to a composition for topical use for treating and improving the aesthetic conditions of the skin, which comprises, as an active ingredient, a mixture of ethyllinoleate and triethylcitrate. This composition is active in the treatment of seborrhea and acne.

12 Claims, No Drawings

COMPOSITION BASED ON ETHYL ESTER OF LINOLEIC ACID AND TRIETHYL ESTER OF CITRIC ACID FOR TOPICAL USE IN THE TREATMENT OF SEBORRHEA AND ACNE

FIELD OF INVENTION

This invention concerns a new product for pharmaceutical and/or cosmetic use in the treatment of acne, acne rosacea and seborrhoea.

PRIOR ART

A very large number of people suffer from acne which has a pathological cutaneous picture characterised by a morphological and functional alteration of the pilosebaceous organ with appearance of whiteheads (closed comedo), blackheads (open comedo), papules and in the more serious forms, pustules, nodules, cysts and scars.

Acne affects about 80% of the population between the ages of 12 and 30 and, above all in women, may persist even to a more advanced age.

The etiopathogenesis of acne is in close relationship with:
an increase in the production of sebum (seborrhoea)
an anomalous keratinisation of the pilosebaceous duct
a bacterial colonization Seborrhoea is a consequence of an exasperated reaction of the sebaceous gland to the action of androgen hormones, to be more exact the action of dihydrotestosterone caused by the reduction of testosterone caused by the enzyme 5-α reductase.

Anomalous keratinisation of the pilosebaceous duct is the direct cause of formation of a keratic plug, cause of formation of microcomedo and later of acne lesions. Due to the increase in production of sebum, and prior to the formation of microcomedo, there is an anomalous growth of cutaneous saprophyte bacteria, such as Propionilbacterium Acnes. The latter, due to the release of lytic enzymes (protease and lipase), capable of destroying the protein structure of the sebaceous gland and to hydrolyse the triglycerides normally contained in the sebum (which besides is produced in larger quantities due to the action of dihydrotestosterone) releasing fatty acids and glycerol. The fatty acids released in this way are characterised by their comedogenic action and are therefore oxidised, forming chemical compounds favouring inflammation.

The therapy used up to now in the pharmaceutical treatment of acne or cosmetic treatment of the seborreha has been mainly based on the action of keratolytic and/or anti-biotic substances, or other active principles, for example, retinoids Among these substances may be mentioned for example salycilic acid, tartaric acid, glycolic acid, resorcin, phenol etc., all capable of carrying out their action aimed at clinically improving the acneic picture through a keratolytic type mechanism.

Among the antibiotic substances used up until now to keep the increase of Propionilbacterium Acnes under control worthy of mention are clindamycine, minocycine, erythromycin, metronidazole, etc.

Other active principles used in treating acne are trans-retinoic acid, found to be efficacious, but characterised by being highly toxic, photo-toxic and teratogenic.

OBJECT AND SUMMARY OF THE INVENTION

The object of the invention is to provide a new product characterised by being highly efficacious with excellent cutaneous tolerability, in particular in the treatment of seborrhoea, acne and acne rosacea.

The object is achieved, according to the invention, with a composition, which is characterised by the fact that it contains as an active ingredient a mixture including the ethyl ester of linoleic acid (ethyllinoleate) and triethylester of citric acid (triethylcitrate).

This composition results as being able, among other things, to inhibit the activity of specific enzymes, such as for example, 5-alpha reductase, lipase and esterase, enabling a control of the seborrhoea and in general the evolution of the acneic and rosacea picture.

DETAILED DESCRIPTION OF THE INVENTION

According to this invention, ethyllinoleate and triethylcitrate can be contained in a composition each in a quantity in weight from between 0.1 to 99.9%, preferably in equal quantities from between 1.00 and 40% each, based on the final weight of the composition.

Furthermore, the composition based on ethyllinoleate and triethylcitrate can also contain various active ingredients, which for descriptive simplicity will be defined as synergists.

The synergists can be chosen from between acetic acid, lactic acid, salicylic acid, tartaric acid, glycolic acid, clindamycin, minocycline, erythromycin, metronidazole, amoxycillin, triclosan, capryloyl glcine, azelaic acid, zinc hydroxide, zinc chloride, vitamin A trans-retinoic acid, resorcinol, hyaluronic acid, gentamicin, meclocycline, phenol, ascorbic acid, tocopherol, lipoic acid, phosphatidyl choline, phosphatidyl serine, chlorhexi-dine, irgasan, adapalene, phospholipids in general, in all the dextrorotary, levorotary forms, racemic mixtures, cis forms, trans forms and relative salts, esters and amides and formulated together with particular additives and excipients for external use.

These synergists may be contained in variable weight quantities from between 0.001 to 90%, such as 0.001 to 70%, preferably from 0.5 to 15% based on the final formulation when the proportions of ethyllinoleate and triethylcitrate are each from between 0.5 to 90.5% in weight.

The clinical efficacy and safety of use are the consequence of an original mechanism of action characterised by the fact that both ethyllinoleate and triethylcitrate, which in themselves behave as inert substances, are transformed into active principles once in contact with the skin. This transformation, from an inert substance into an active principle is a result of the hydrolysis, which takes place through specific cutaneous enzymes or bacteria (lipase and esterase) capable of releasing ethyl alcohol and respectively linolenic acid, diethyl citrate then monoethyl citrate and finally citric acid.

The action mechanism of the composition of the invention can be described more in detail as follows.

Ethyllinoleate and triethylcitrate synergically are able to reduce seborrhoea and hyper keratinisation of the pilosebaceous duct; this action is achieved through the release of the respective acid forms, through hydrolysis of the esters by the action of the lipase bacteria.

In this invention it has been proven that hydrolysis of ethyllinoleate and triethylcitrate carried out by lipase bacteria is to be preferred to hydrolysis of the triglycerides (lipid component of sebum) carried out by the same lipase bacteria, consequently avoiding an irritative condition due to the release of fatty acids achieved through hydrolysis of the triglycerides.

In relation to hyper keratinisation of the pilosebaceous duct, the combined action of ethyllinoleate and triethylcitrate is innovative in that the former prevents hyper-keratinisation whereas the latter cures it, behaving as a keratolytic. This combined action results in higher efficacy compared with the effect of the two components taken individually.

In relation to seborrhoea the combined action of ethyllinoleate and triethylcitrate is innovative in that it results in a decrease in the sebum levels achieved by inhibiting the 5-alpha reductase enzyme, an enzyme which as stated above is the cause of the reduction of testosterone to dihydrotestosterone whose action is capable of increasing the production of sebum. Once ethyllinoleate is hydrolysed into linoleic acid, it is able to inhibit the activity of 5-alpha reductase by a direct mechanism, whereas triethylcitrate, once hydrolysed into citric acid, acts in an indirect way, creating an environment where the activity of the aforementioned enzyme is obstructed.

In other words, lipase bacteria recognise the ethyllinoleate and triethylcitrate mixture as the preferential substratum rather than the triglycerides of the sebum and so do not interfere with the structure of these triglycerides, thus reducing the inflammatory pathologies of seborrhoea and acne.

EFFECTS OF THE INVENTION IN RELATION TO TESTS RESERVED ON SAMPLES

Based on the present invention, tests were carried out to evaluate experimentally the action of two products, a lotion and a cream, for the treatment of acne through a clinical test using a sebumetric measuring device.

Aim

The test is able to evaluate if the products being tested are a valid help in the treatment against acne and if they are able to mitigate reddening due to the presence of acne focus.

Test Specimen

Five female volunteers from between 15 and 28 years of age with greasy skin and suffering from acne.

Preparation of Samples

The samples must be applied, on the basis of their use characteristics, as they are.

Method of Application of Samples

The samples must be applied uniformly on specific parts of the face, according to the indications given on the description card handed to the volunteer.

The lotion on the right side of the face; the cream on the left side of the face.

Carrying Out the Test

After finding the volunteers for the test, the following instrumental evaluations are carried out:

basic sebum measurement using an authorized sebumetric device in compliance with EEC regulations (SKIN LAB®)

Basic hydration using an authorized instrument in compliance with EEC regulations (SKIN LAB®)

Basic TEWL using an authorized instrument in compliance with EEC regulations (Tewameter®)—only on the left side of the face Acquisition of micro photographs using a video camera with polarised light—VIDEOCAP—with 20× enlargements and, when possible, 200×. The micro images are necessary to visualise in depth the slight blemishes due to acne and to highlight any improvements during the treatment under examination.

Acquisition of macro photographs with Mini DV. The photographs are useful in defining the general start situation and to document any macroscopic improvements during the use of the products.

Furthermore the volunteers are supplied with a card on which to register daily observations about the cosmetic agreeable nature of the products and their performance.

Each volunteer is given a card describing how she must apply the various products being tested. To facilitate the task, the first application is carried out on the premises.

The following controls are carried out after seven days (t7), fourteen days (t14), twenty one days (t21) and twenty eight days (t28) of treatment with a lotion and a cream.

Following the above experiment, the difference between the sebumetric, keratic and TEWL values measured before and after the application of the products using the polarised light video camera and with the Mini DV the variations of the furuncles and acne pustules was evaluated.

The sebumetric, keratic and TEWL values are registered, elaborated and graphically presented together with the results in the following tables.

TABLES AND GRAPHIC REPRESENTATION OF THE RESULTS
Sebometric values after prolonged use
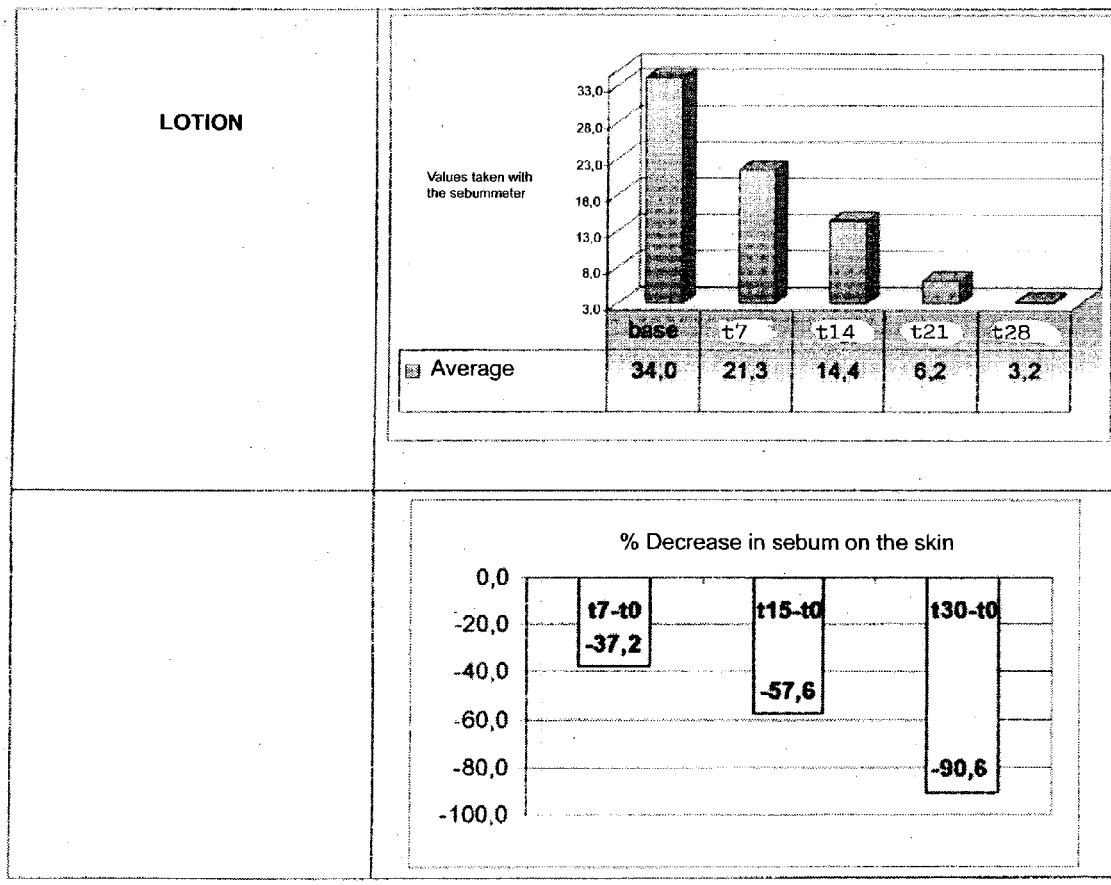

Hydration indexes after prolonged use
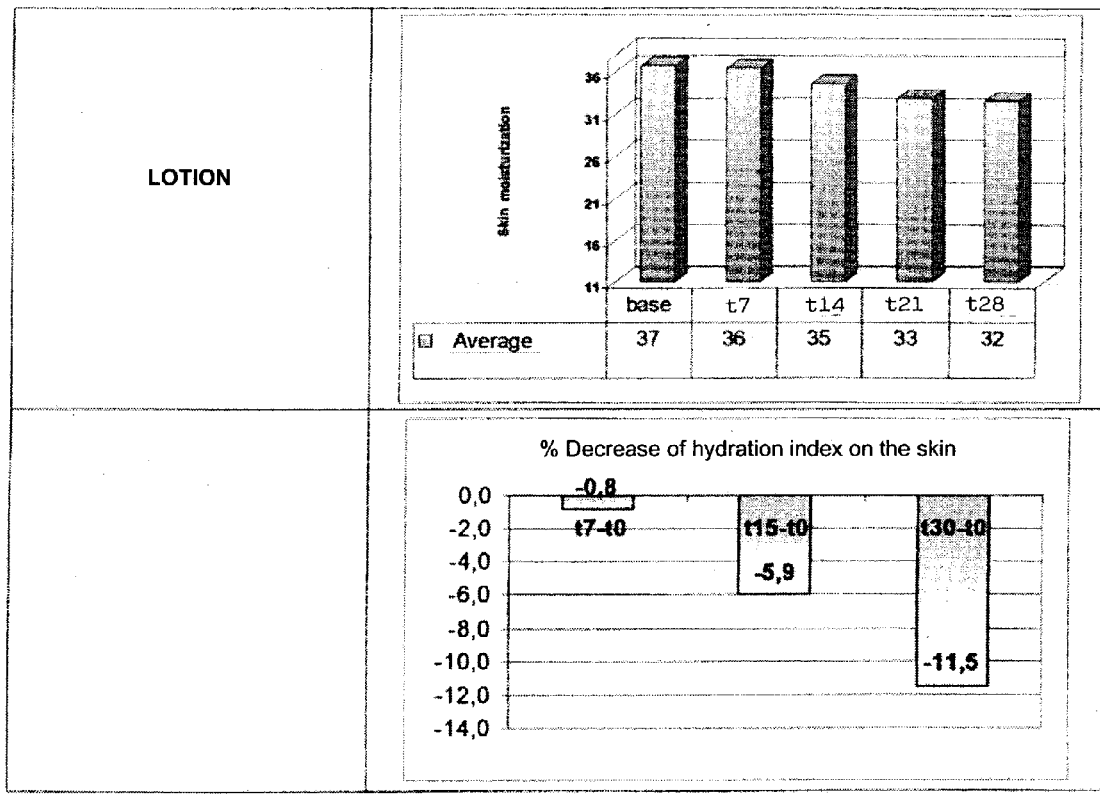

Sebometric values after prolonged use
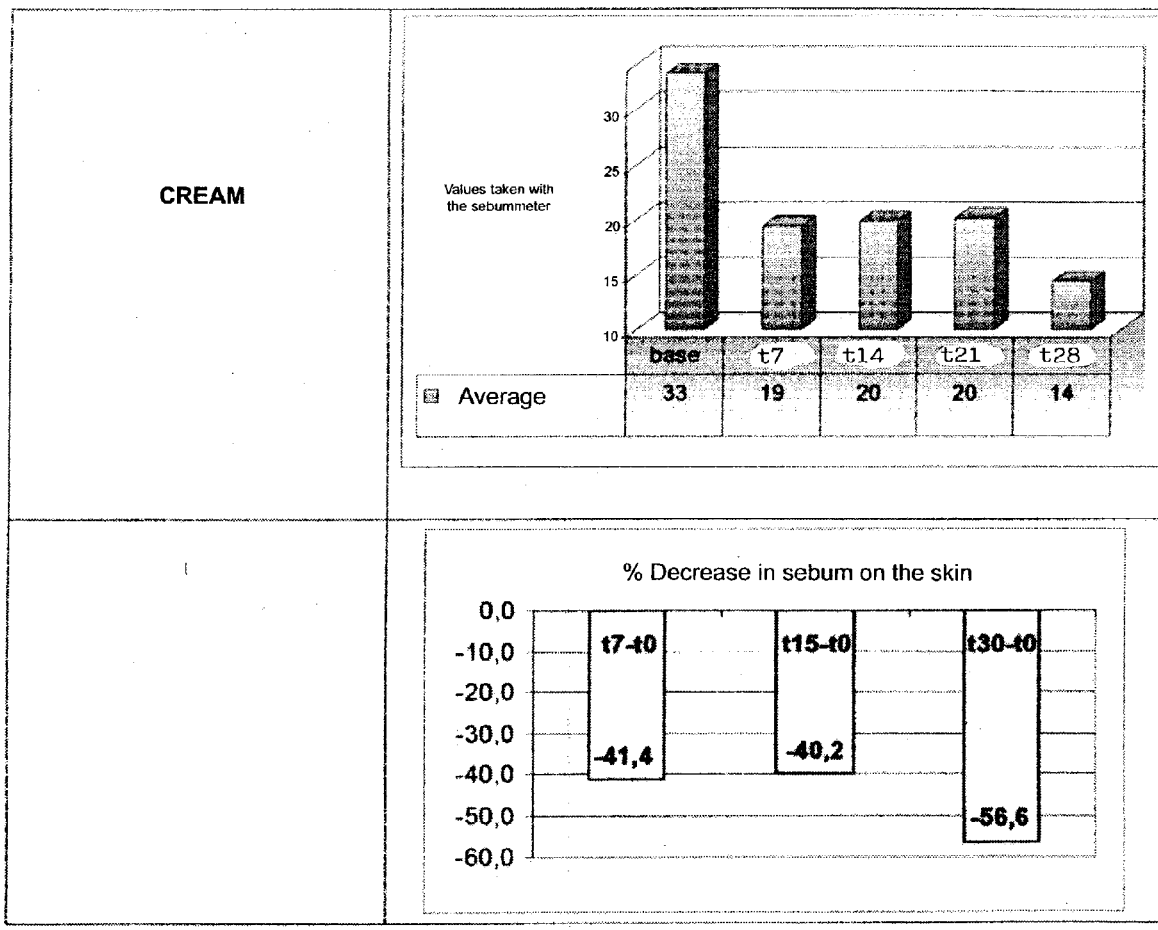

Hydration indexes after prolonged use
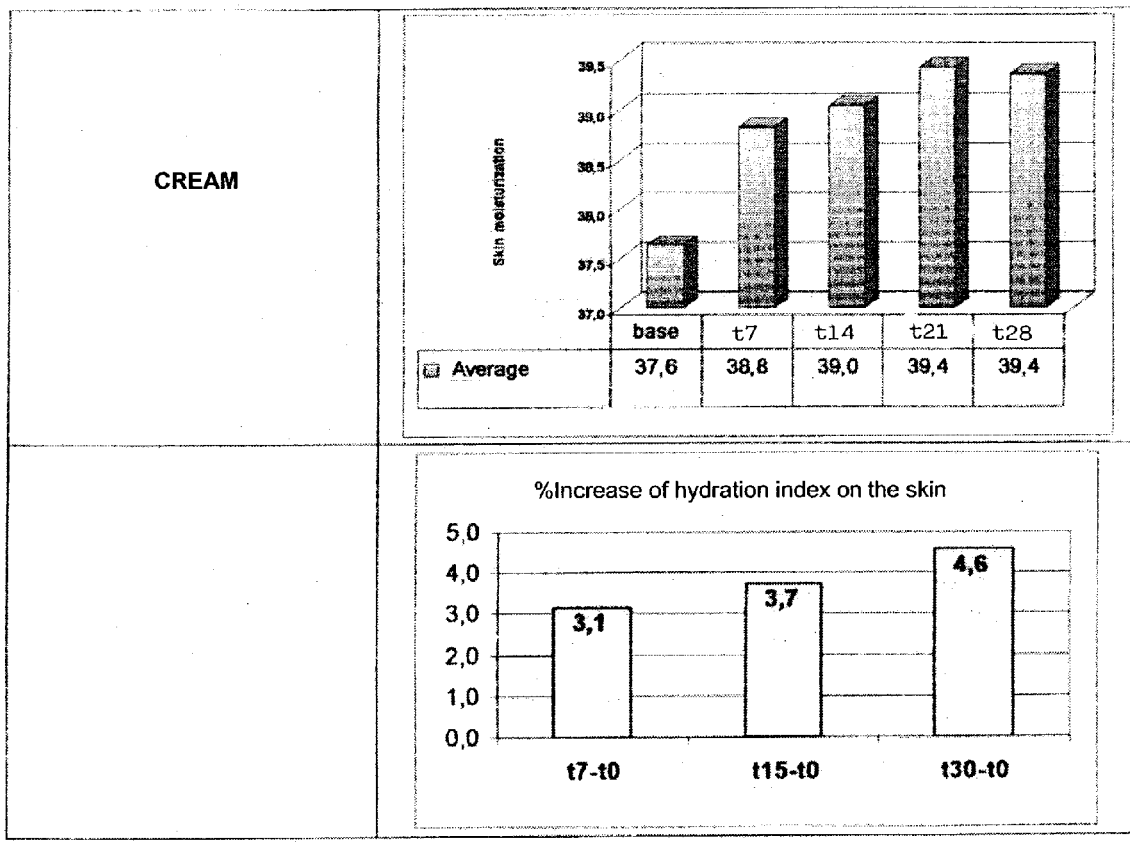

TEWL values after prolonged use
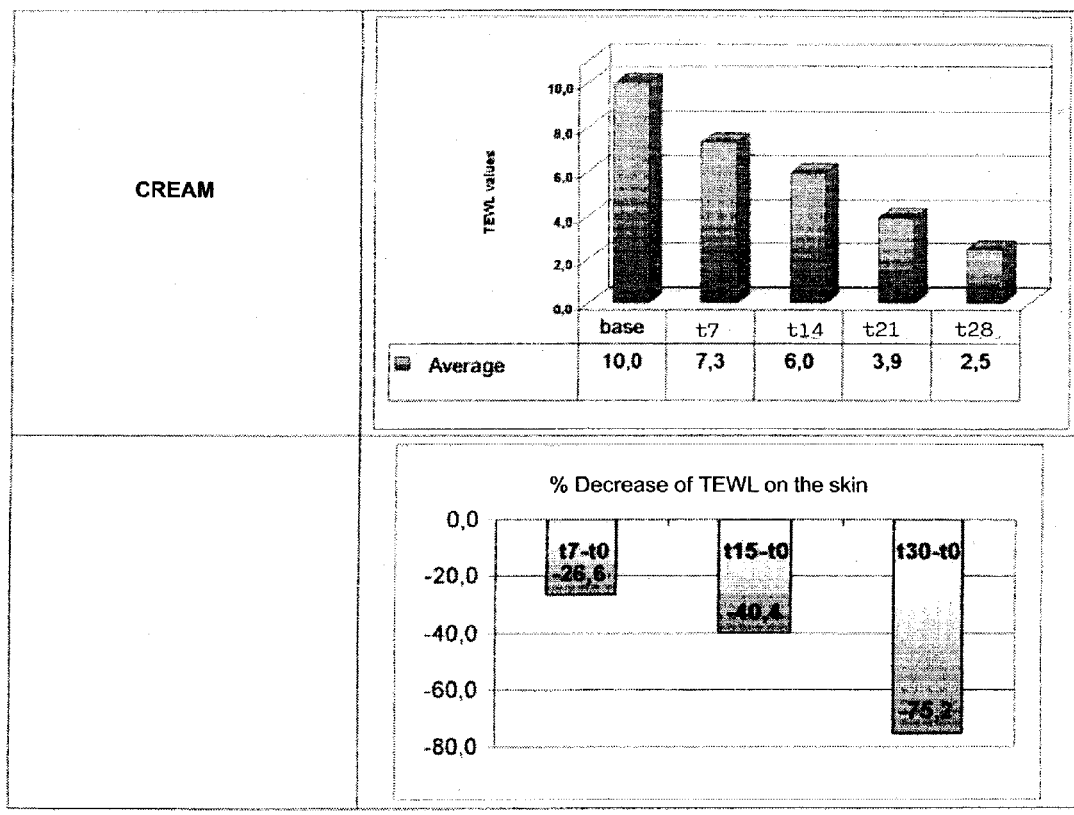

EXAMPLES OF FORMULATION

Here following are some examples of formulations according to the present invention.

Preparation 01—Oleolita

| N° | Description | % w/w |
|----|-------------|-------|
| 01 | Ethyllinoleate | 20.00 |
| 02 | Triethylcitrate | 80.00 |

Method of preparation: mix 01 in 02

Preparation 02—Alcoholic Solution

| N° | Description | % w/w |
|----|-------------|-------|
| 01 | Ethyllinoleate | 20.00 |
| 02 | triethylcitrate | 20.00 |
| 03 | salicyclic acid | 2.00 |
| 04 | ethyl acid | 58.00 |

Method of preparation: dissolve 03 in 04; to the solution mix 01+02

Preparation 03—Emulsion

| N° | Description | % w/w |
|----|-------------|-------|
| | PHASE A | |
| 01 | Ethyllinoleate | 5.00 |
| 02 | triethylcitrate | 5.00 |
| 03 | Ascorbil palmitate | 1.50 |
| 04 | Ppg - 15 stearyl ether | 10.00 |
| 05 | Capryloyl glycine | 4.00 |
| 06 | Steareth - 2 | 3.00 |
| 07 | Steareth - 21 | 2.00 |
| | PHASE B | |
| 08 | Preservatives | as req. |
| 09 | Glycerol | 3.0 |
| 10 | Water | as req. |

Method of preparation: Phase A, mix 01+02+03+04+05+06+07 and heat to 75° C.; Phase B, mix 08+09+10 and heat the pre-mix to +75%C., then add under agitation the Phase B to Phase A. Cool to room temperature always agitating.

Preparation 04—Alcoholic Solution

| N° | Description | % w/w |
|----|-------------|-------|
| 01 | Ethyllinoleate | 20.00 |
| 02 | Triethylcitrate | 20.00 |
| 03 | Erythromycin | 10.00 |
| 04 | ethyl acid | 50.00 |

Method of preparation: dissolve 03 in 04, mix 01+02 in the solution

Preparation 05—Alcoholic Solution

| N° | Description | % w/w |
|----|-------------|-------|
| 01 | Trans-retinoic | 0.025 |
| 02 | ethyllinoleate | 5.00 |
| 03 | triethylcitrate | 20.00 |
| 04 | ethylic acid | as. req. |

Method of preparation: dissolve 01+02+03+in 04

Preparation 06—Alcoholic Solution

| N° | Description | % w/w |
|----|-------------|-------|
| 01 | clindamycin | 1.00 |
| 02 | ethyllinoleate | 5.00 |
| 03 | triethylcitrate | 20.00 |
| 04 | ethyl acid | as req. |

Method of preparation: mix 02+03+04 then dissolve 01 in it.

It has therefore been proved that the action of ethyllinoleate and triethylcitrate, described in the treatment of acne, greasy skin and seborrhoea, in consideration of the particular biological, pharmacological, physiological and biochemical action mechanism, has been found to be wider and is addressed to the treatment of several other cutaneous pathologies such as for example atopic dermatitis, dermatitis seborrheica, exfoliative dermatitis, stasis dermatitis, neurodermatitis, acne, acne rosacea, alopecia areata, scarring alopecia, female alopecia, anagen effluviam, Hippocratic alopecia, psoriasis, Lichen, ichthyosis, xerodermia, keratosis pilaris, decubital ulcer, trophic ulcer, torpid sores, angioma nevus or vascular bundle, hemangioma, granuloma telangiectaticum, keratosis seborrhoea, etc.

The use of ethyllinoleate and triethylcitrate, also combined with opportune synergists, due to its particular action mechanism on the skin is innovative even as regards to its cosmetic use, such as: anti-aging composition aimed at improving the aesthetic conditions of the skin and to prevent signs of cutaneous aging; anti-wrinkle; moisturiser; the treatment of cutaneous hyper-pigmentation; cosmetic treatment of seborrhoea with tendency to develop into acne.

The composition is prepared in formulations for external use, such as in the form of water emulsions in oil, oil emulsions in water, mono-phase solutions, dual-phase pseudo-solutions, mono-phase gels, dual-phase gels, sub-micelle gels, anhydrous ointments, powder sprinklers, alcoholates, alcohol solutions, and hydro-alcoholic solutions.

The invention claimed is:

1. Composition for topical use for treating and improving the aesthetic condition of the skin consisting essentially of, as active ingredient, a mixture of ethyl linoleate and triethyl citrate.

2. Composition of claim 1 wherein the ethyl linoleate is contained in a quantity of about 0.1 to 99.9% weight/weight of the composition and the triethyl citrate is contained in a quantity of about 99.9 to 0.1% weight/weight of the composition.

3. Composition of claim 1 wherein the composition is prepared for external use in the form of a member selected from the group consisting of a water emulsion in oil, an oil emulsion in water, a mono-phase solution, a dual-phase pseudo-solution, a mono-phase gel, a dual-phase gel, a sub-micelle gel, an anhydrous ointment, a powder sprinkler, an alcoholate, an alcohol solution, and a hydro-alcoholic solution.

4. Composition of claim 3 wherein the ethyl linoleate is contained in a quantity of about 0.1 to 99.9% weight/weight of the composition and the triethyl citrate is contained in a quantity of about 99.9 to 0.1% weight/weight of the composition.

5. Composition of claim 2 wherein the ethyl linoleate is contained in a quantity of about 1 to 40% weight/weight of the composition and the triethyl citrate is contained in a quantity of about 1 to 40% weight/weight of the composition.

6. Composition of claim 4 wherein the ethyl linoleate is contained in a quantity of about 1 to 40% weight/weight of the composition and the triethyl citrate is contained in a quantity of about 1 to 40% weight/weight of the composition.

7. Composition of claim 1 wherein the composition further contains at least one additive selected from the group consisting of acetic acid, lactic acid, salicylic acid, tartaric acid, glycolic acid, clindamycin, minocycline, erythromycin, metronidazole, amoxycillin, triclosan, capryloyl glcine, azelaic acid, zinc hydroxide, zinc chloride, vitamin A trans-retinoic acid, resorcinol, hyaluronic acid, gentamicin, meclocycline, phenol, ascorbic acid, tocopherol, lipoic acid, phosphatidyl choline, phosphatidyl serine, chlorhexidine, irgasan, adapalene, and the dextrorotary forms, levorotary forms, racemic mixtures, cis forms, trans forms, salts, esters and amides thereof, in an excipient for external use.

8. Composition of claim 7 wherein the ethyl linoleate is contained in a quantity of about 1 to 40% weight/weight of the composition and the triethyl citrate is contained in a quantity of about 1 to 40% weight/weight of the composition, and the at least one additive is contained in a quantity of about 0.001 to 90% weight/weight of the composition.

9. Composition of claim 7 wherein the at least one additive is contained in a quantity of about 0.5 to 15% weight/weight of the composition.

10. Composition of claim 1 wherein the composition further contains a phospholipid.

11. Composition for topical use for treating and improving the aesthetic condition of the skin consisting essential-ly of, as active ingredient, a mixture of ethyl linoleate and triethyl citrate; and
wherein the composition further contains at least one additive selected from the group consisting of acetic acid, lactic acid, salicylic acid, tartaric acid, glycolic acid, clindamycin, minocycline, erythromycin, metronidazole, amoxycillin, triclosan, capryloyl glcine, azelaic acid, zinc hydroxide, zinc chloride, vitamin A trans-retinoic acid, resorcinol, hyaluronic acid, gentamicin, meclocycline, phenol, ascorbic acid, tocopherol, lipoic acid, phosphatidyl choline, phosphatidyl serine, chlorhexidine, irgasan, adapalene, and the dextrorotary forms, levorotary forms, racemic mixtures, cis forms, trans forms, salts, esters and amides thereof; and
wherein the composition is prepared for external use in the form of a member selected from the group consisting of a water emulsion in oil, an oil emulsion in water, a mono-phase solution, a dual-phase pseudo-solution, a mono-phase gel, a dual-phase gel, a sub-micelle gel, an anhydrous ointment, a powder sprinkler, an alcoholate, an alcohol solution, and a hydro-alcoholic solution.

12. Composition of claim 11 wherein the ethyl linoleate is contained in a quantity of about 1 to 40% weight/weight of the composition and the triethyl citrate is contained in a quantity of about 1 to 40% weight/weight of the composition, and the at least one additive is contained in a quantity of about 0.001 to 90% weight/weight of the composition.

* * * * *